(12) United States Patent
Uchida

(10) Patent No.: US 12,367,988 B2
(45) Date of Patent: Jul. 22, 2025

(54) IMAGE DISPLAY APPARATUS, IMAGE DISPLAY SYSTEM, IMAGE DISPLAY METHOD, AND NON-TRANSITORY COMPUTER READABLE MEDIUM

(71) Applicant: NEC Corporation, Tokyo (JP)

(72) Inventor: Terutaka Uchida, Tokyo (JP)

(73) Assignee: NEC CORPORATION, Tokyo (JP)

( * ) Notice: Subject to any disclaimer, the term of this patent is extended or adjusted under 35 U.S.C. 154(b) by 120 days.

(21) Appl. No.: 18/265,369

(22) PCT Filed: Nov. 5, 2021

(86) PCT No.: PCT/JP2021/040795
§ 371 (c)(1),
(2) Date: Jun. 5, 2023

(87) PCT Pub. No.: WO2022/130822
PCT Pub. Date: Jun. 23, 2022

(65) Prior Publication Data
US 2024/0038403 A1 Feb. 1, 2024

(30) Foreign Application Priority Data

Dec. 14, 2020 (JP) .................. 2020-206504

(51) Int. Cl.
*G16H 80/00* (2018.01)
*A61B 5/01* (2006.01)
(Continued)

(52) U.S. Cl.
CPC ............ *G16H 80/00* (2018.01); *A61B 5/1113* (2013.01); *A61B 5/1128* (2013.01);
(Continued)

(58) Field of Classification Search
CPC ........ G16H 80/00; G16H 20/00; G16H 30/40; G16H 50/80; A61B 5/1113; A61B 5/1128;
(Continued)

(56) References Cited

U.S. PATENT DOCUMENTS

2008/0080748 A1* 4/2008 Sukegawa .............. G06V 40/10
382/118
2017/0109871 A1* 4/2017 Nakano ..................... G06T 7/11
(Continued)

FOREIGN PATENT DOCUMENTS

CN 111554366 A 8/2020
CN 111863272 A 10/2020
(Continued)

OTHER PUBLICATIONS

International Search Report for PCT Application No. PCT/JP2021/040795, mailed on Feb. 8, 2022.
(Continued)

*Primary Examiner* — Santiago Garcia
(74) *Attorney, Agent, or Firm* — Sughrue Mion, PLLC

(57) ABSTRACT

An image display apparatus comprises at least one memory storing instructions, and at least one processor configured to execute the instructions to acquire a plurality of pieces of image data from a camera, identify a person from the image data, estimate a possibility of the person identified from the image data having developed an infectious disease, detect an image of interest including a person of interest regarding which there is the possibility of the person of interest having developed an infectious disease and a nearby person present in the vicinity of the person of interest based on a result of the estimation, extract a series of images including the image of interest, and display the extracted series of images.

19 Claims, 11 Drawing Sheets

(51) Int. Cl.
- *A61B 5/11* (2006.01)
- *G06T 7/00* (2017.01)
- *G06V 20/52* (2022.01)
- *G06V 40/16* (2022.01)
- *G06V 40/20* (2022.01)

(52) U.S. Cl.
CPC ............ *G06T 7/0016* (2013.01); *G06V 20/52* (2022.01); *G06V 40/166* (2022.01); *G06V 40/172* (2022.01); *G06V 40/20* (2022.01); *A61B 5/015* (2013.01); *G06T 2207/10048* (2013.01); *G06V 2201/07* (2022.01)

(58) Field of Classification Search
CPC ................. A61B 5/015; G06T 7/0016; G06T 2207/10048; G06V 20/52; G06V 40/166; G06V 40/172; G06V 40/20; G06V 2201/07

See application file for complete search history.

(56) References Cited

U.S. PATENT DOCUMENTS

| | | | | |
|---|---|---|---|---|
| 2018/0012373 | A1* | 1/2018 | Ozaki | ..................... H04N 23/90 |
| 2019/0349554 | A1 | 11/2019 | Derenne et al. | |
| 2020/0394419 | A1 | 12/2020 | Takayanagi | |
| 2021/0271896 | A1* | 9/2021 | Yano | ..................... G06V 20/52 |
| 2021/0275034 | A1* | 9/2021 | Frank | ..................... G01J 5/0265 |
| 2021/0327562 | A1* | 10/2021 | Kushwah | .............. G06T 7/0016 |
| 2022/0208387 | A1* | 6/2022 | Kawabata | .............. G16H 30/40 |
| 2023/0135198 | A1* | 5/2023 | Osborne | ................ G06Q 20/18 705/16 |
| 2024/0005645 | A1* | 1/2024 | Cha | ........................ G06T 7/0002 |

FOREIGN PATENT DOCUMENTS

| | | |
|---|---|---|
| JP | 2003-122855 A | 4/2003 |
| JP | 2012-235415 A | 11/2012 |
| JP | 2013-176471 A | 9/2013 |
| JP | 2016-103786 A | 6/2016 |
| JP | 2016-184196 A | 10/2016 |
| JP | 2018-036872 A | 3/2018 |
| JP | 2019-036184 A | 3/2019 |
| JP | 2019-083395 A | 5/2019 |
| JP | 2019-200503 A | 11/2019 |
| JP | 2022-029759 A | 2/2022 |
| JP | 2022-064128 A | 4/2022 |
| WO | 2019/239813 A1 | 12/2019 |

OTHER PUBLICATIONS

JP Office Action for JP Application No. 2022-569762, mailed on Jul. 30, 2024 with English Translation.

Japanese Office Action for JP Application No. 2022-569762 mailed on Dec. 24, 2024 with English Translation.

* cited by examiner

IMAGE DISPLAY APPARATUS, IMAGE DISPLAY SYSTEM, IMAGE DISPLAY METHOD, AND NON-TRANSITORY COMPUTER READABLE MEDIUM

This application is a National Stage Entry of PCT/JP2021/040795 filed on Nov. 5, 2021, which claims priority from Japanese Patent Application 2020-206504 filed on Dec. 14, 2020, the contents of all of which are incorporated herein by reference, in their entirety.

TECHNICAL FIELD

The present invention relates to an image display apparatus, an image display system, an image display method, and a non-transitory computer readable medium.

BACKGROUND ART

There has been a growing demand to know the risk of being infected with an infectious disease for a plurality of people present in a predetermined area. As means for realizing such a demand, it is considered that, for example, estimating a person's physical condition and then visually recognizing a contact state and the like between the aforementioned person and those around this person in an area where this person is present is effective. Therefore, a technique for recognizing a person exhibiting a symptom of an infectious disease and detecting the possibility of a close contact between the aforementioned person and those around this person is required.

In relation to the aforementioned technology, for example, Patent Literature 1 discloses a system that recognizes changes in a user's physical condition. In the technology disclosed in Patent Literature 1, when the past measurement data of a specific user does not fall within a predetermined range, similar measurement data that is similar to the latest measurement data is retrieved from among pieces of the past measurement data of users other than the specific user, and diseases or symptoms that the specific user may suffer in the near future are estimated.

Further, Patent Literature 2 discloses a hospital infection influence range viewing system. This system includes a round route device, a round log recording terminal, a log analysis unit, and a map display unit. The round route device is disposed in a medical facility, and the round log recording terminal records round information about a person from records of communication with the round route device. The log analysis unit calculates the degree of risk of the person being infected by analyzing the round information based on a preset analysis rule. Further, the map display unit displays the infection influence range in the medical facility based on preset map information, a movement route of the person obtained from the round information, and the degree of risk of the person being infected.

Patent Literature 3 discloses a home treatment patient relief system including a monitor center connected to medical equipment used by a home treatment patient through communication means and a database that stores personal information of the home treatment patient. The monitor center detects a state of the medical equipment used by the home treatment patient for each predetermined period, and in the event of a disaster, it retrieves the database and creates a list of relief priorities in order of severity.

CITATION LIST

Patent Literature

Patent Literature 1: Japanese Unexamined Patent Application Publication No. 2019-036184
Patent Literature 2: Japanese Unexamined Patent Application Publication No. 2016-184196
Patent Literature 3: Japanese Unexamined Patent Application Publication No. 2003-122855

SUMMARY OF INVENTION

Technical Problem

However, even when the above techniques are combined, it is difficult to track all the movements of people exhibiting symptoms of an infectious disease in a place where many people come and go.

The present disclosure has been made in view of the above-described problem and an object thereof is to provide an image display apparatus and the like which suitably display a situation in which a risk of infection is high.

Solution to Problem

An image display apparatus according to an example embodiment of the present disclosure includes image data acquisition means, identification means, estimation means, image of interest detection means, and output means. The image data acquisition means acquires a plurality of pieces of image data from a camera. The identification means identifies a person from the image data. The estimation means estimates a possibility of the person identified from the image data having developed an infectious disease. The image of interest detection means detects an image of interest including a person of interest regarding which there is the possibility of the person of interest having developed an infectious disease and a nearby person present in the vicinity of the person of interest based on a result of the estimation. The output means extracts a series of images including the image of interest and displays the extracted series of images.

In a method according to an example embodiment of the present disclosure, a computer executes the following method. The computer acquires a plurality of pieces of image data from a camera. The computer identifies a person from the image data. The computer estimates a possibility of the identified person having developed an infectious disease. The computer detects an image of interest including a person of interest regarding which there is the possibility of the person of interest having developed an infectious disease and a nearby person present in the vicinity of the person of interest based on a result of the estimation. The computer extracts a series of images including the image of interest.

A program according to an example embodiment of the present disclosure causes a computer to execute the following steps. The computer acquires a plurality of pieces of image data from a camera. The computer identifies a person from the image data. The computer estimates a possibility of the identified person having developed an infectious disease. The computer detects an image of interest including a person of interest regarding which there is the possibility of the person of interest having developed an infectious disease and a nearby person present in the vicinity of the person of interest based on a result of the estimation. The computer extracts a series of images including the image of interest.

Advantageous Effects of Invention

According to the present disclosure, it is possible to provide an image display apparatus and the like which suitably display a situation in which a risk of infection is high.

EXAMPLE EMBODIMENT

Figure 1:
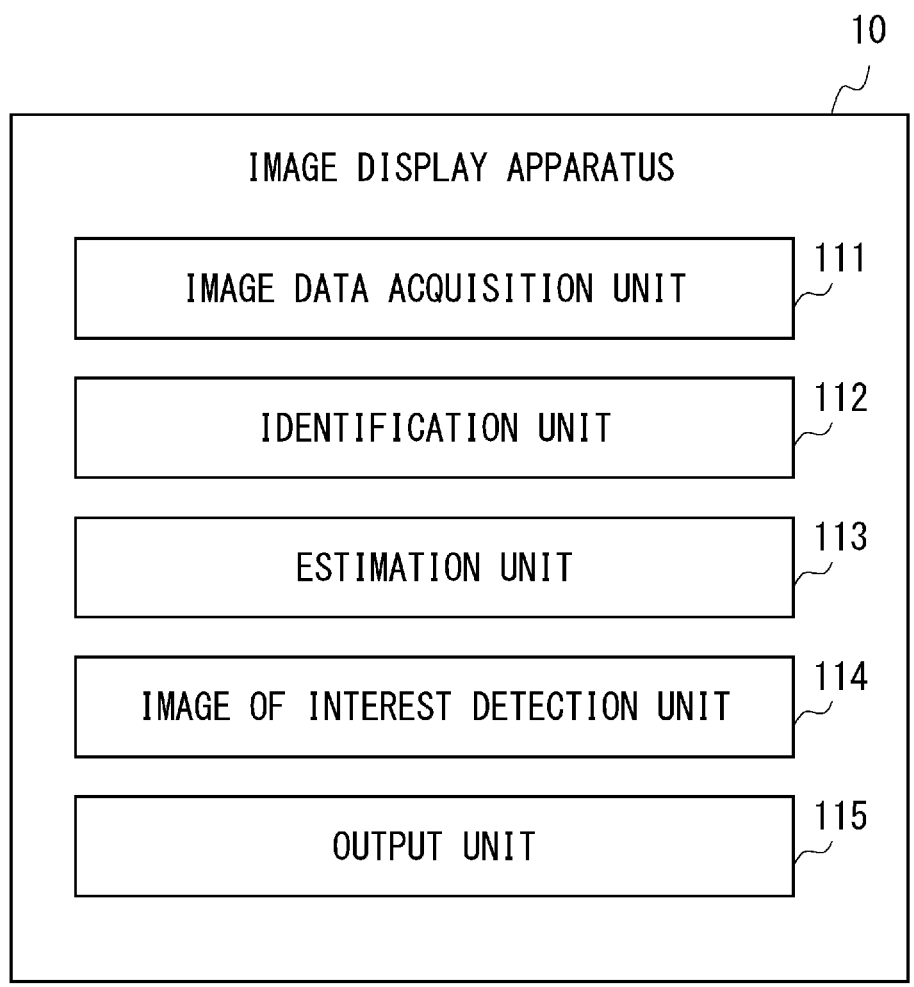
FIG. 1 is a block diagram of an image display apparatus according to a first example embodiment.

The present invention will be described hereinafter through example embodiments of the present invention. However, the following example embodiments are not intended to limit the scope of the invention according to the claims. Further, all the components described in the example embodiments are not necessarily indispensable as means for solving the problem. For the clarification of the description, the following descriptions and the drawings are partially omitted and simplified as appropriate. Note that the same elements are denoted by the same reference numerals or symbols throughout the drawings, and redundant descriptions are omitted as necessary.

First Example Embodiment

Example embodiments of the present invention will be described below with reference to the drawings. FIG. 1 is a block diagram of an image display apparatus 10 according to a first example embodiment. The image display apparatus 10 shown in FIG. 1 is connected to a camera installed in a predetermined facility or outdoors, acquires image data captured by the camera, and displays an image or a group of images of interest. The image display apparatus 10 mainly includes an image data acquisition unit 111, an identification unit 112, an estimation unit 113, an image of interest detection unit 114, and an output unit 115.

The image data acquisition unit 111 acquires a plurality of pieces of image data from the camera. The plurality of pieces of image data are pieces of image data captured at different times. For example, a camera captures images of 30 frames of per second and supplies image data of these captured images to the image data acquisition unit 111. One or a plurality of cameras may be connected to the image data acquisition unit 111. Further, the camera to which the image data acquisition unit 111 is connected may be fixed in order to capture a predetermined angle of view, or may be a movable camera that pans, tilts, or zooms. The image data acquisition unit 111 supplies image data acquired from the camera to at least the identification unit 112. The image data acquisition unit 111 also supplies image data acquired from the camera to other components as appropriate.

The identification unit 112 receives image data from the image data acquisition unit 111 and identifies a person from the received image data. More specifically, for example, the identification unit 112 extracts a feature value of the received image data and detects a feature value of the person. The identification unit 112 supplies data (identification data) about the identified person to the estimation unit 113.

The estimation unit 113 receives the identification data from the identification unit 112 and estimates a possibility of the identified person having developed an infectious disease by using the received identification data. More specifically, for example, the estimation unit 113 receives data indicating the states of physical actions performed by the person as the feature values, and detects that the identified person exhibits symptomatic actions related to the development of an infectious disease. The symptomatic actions related to the development of an infectious disease are actions such as coughing, sneezing, putting a hand on the buttocks, and putting a hand on the chest. The estimation unit 113 estimates whether or not there is a possibility of the identified person having developed an infectious disease. In this case, the estimation unit 113 may estimate that the identified person may possibly have developed an infectious disease when the identified person is performing a preset action. Alternatively, the estimation unit 113 may estimate whether or not the possibility of the identified person having developed an infectious disease is greater than or equal to a preset threshold based on a plurality of actions performed by the identified person. The estimation unit 113 supplies a result of the above estimation to the image of interest detection unit 114.

The image of interest detection unit 114 detects, using the result of the estimation received from the estimation unit 113, an image including a person of interest who may possibly have developed an infectious disease from the plurality of pieces of image data acquired by the image data acquisition unit 111. Note that the "person of interest" refers to a person who the estimation unit 113 has estimated may possibly have developed an infectious disease. Further, the image of interest detection unit 114 detects an image of interest including the person of interest and a nearby person from the plurality of pieces of image data acquired by the image data acquisition unit 111.

Note that the "nearby person" refers to, for example, a person present at a position from which a distance between this person and the person of interest is shorter than a preset value. However, the definition of the nearby person is not limited thereto. For example, the nearby person may be a person present at a position from which a distance between this person and the person of interest is shorter than a preset value and present at the position for a preset period or longer. That is, the nearby person is a person who is present near the person of interest and to whom an infectious disease may be transmitted from the person of interest. The image of interest detection unit 114 determines a situation in which an infectious disease may be transmitted from the person of interest to the nearby person as a situation in which a risk of infection is high, and detects the captured image as an image of interest. When the image of interest detection unit 114 detects the image of interest, the image of interest detection unit 114 supplies data related to the image of interest to the output unit 115.

The output unit 115 receives data related to the image of interest from the image of interest detection unit 114 and extracts a series of images including the image of interest from the received data. The output unit 115 extracts, for example, a group of images including the image of interest for a preset period. The preset period is, for example, five seconds, 10 seconds, or 30 seconds before and after the capturing of the image of interest. Note that, in the present disclosure, a "group of images" refers to images captured continuously. Therefore, the "group of images" may be referred to as a "moving image". The output unit 115 outputs the extracted group of images to a predetermined display apparatus to which the output unit 115 is connected.

The configuration of the image display apparatus 10 has been described above. By the above-described configuration, the image display apparatus 10 can detect a person who is suspected of having developed an infectious disease from image data acquired from the camera, and extract a group of images indicating that the infectious disease may have been transmitted to a person present in the vicinity of the above person and display it.

Figure 2:
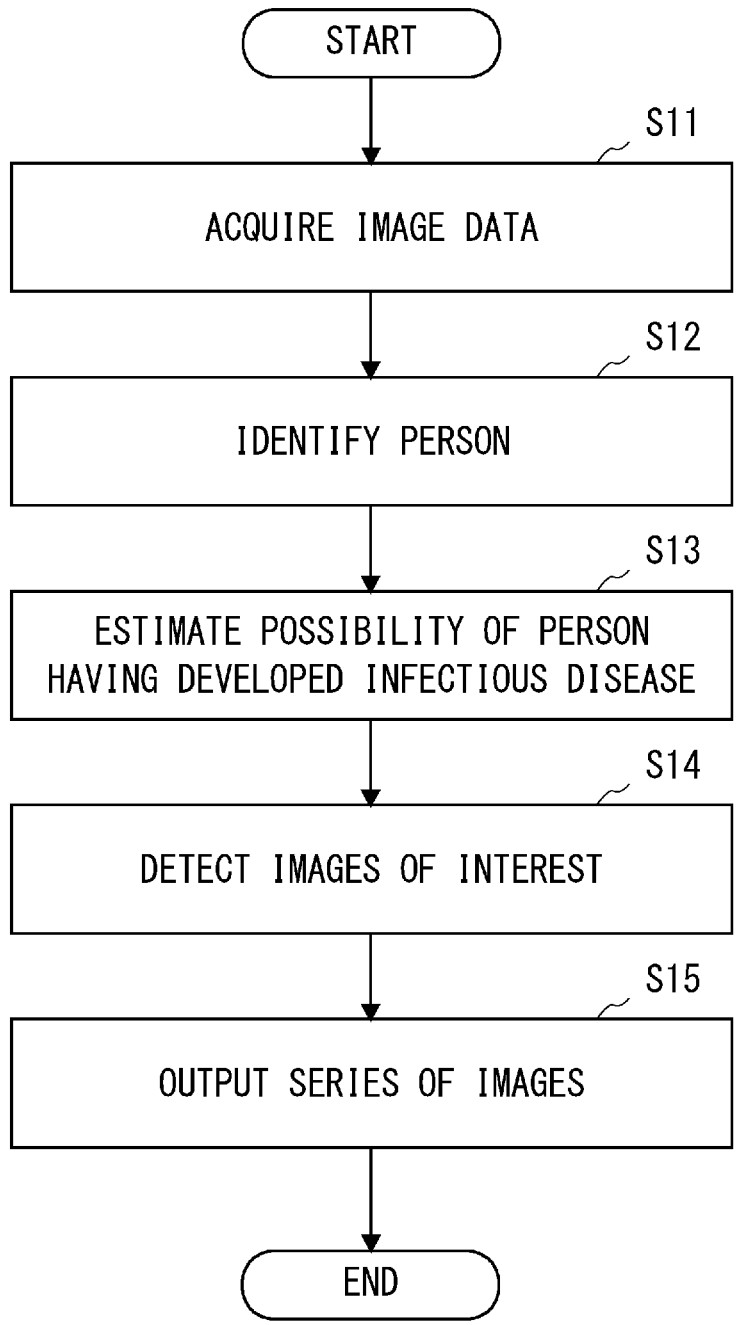
FIG. 2 is a flowchart showing an image display method according to the first example embodiment.

Next, an image display method executed by the image display apparatus 10 will be described with reference to FIG. 2. FIG. 2 is a flowchart showing an image display method according to the first example embodiment. The flowchart shown in FIG. 2 is started, for example, when the image display apparatus 10 is activated.

First, the image data acquisition unit 111 acquires a plurality of pieces of image data from the camera (Step S11). The image data acquisition unit 111 supplies the plurality of pieces of acquired image data to at least the identification unit 112.

Next, the identification unit 112 receives the image data from the image data acquisition unit 111 and identifies a person from the received image data (Step S12). When the identification unit 112 identifies the person, it supplies identification data to the estimation unit 113.

Next, the estimation unit 113 estimates a possibility of the identified person having developed an infectious disease by using the identification data received from the identification unit 112 (Step S13). The estimation unit 113 supplies a result of the estimation to the image of interest detection unit 114.

Next, the image of interest detection unit 114 detects, from the result of the estimation received from the estimation unit 113, images of interest including the person of interest regarding which there is a possibility of the person of interest having developed an infectious disease and a nearby person present in the vicinity of the person of interest (Step S14). The image of interest detection unit 114 supplies the detected images of interest to the output unit 115.

Next, the output unit 115 extracts a series of images including the image of interest from the images of interest received from the image of interest detection unit 114, and outputs the extracted series of images to a predetermined display apparatus (Step S15).

The image display apparatus according to the first example embodiment has been described above. Note that the image display apparatus 10 includes a processor and a storage device as components that are not shown. The storage device included in the image display apparatus 10 includes, for example, a storage device including a non-volatile memory such as a flash memory or a Solid State Drive (SSD). In this case, the storage device included in the image display apparatus 10 stores a computer program (hereafter also referred to simply as a program) for executing the image display method described above. Further, the processor loads a computer program from the storage device into a buffer memory such as a Dynamic Random Access Memory (DRAM) and executes the loaded program.

Each of the components included in the image display apparatus 10 may be implemented by dedicated hardware. Further, some or all of the components may be implemented by general-purpose or dedicated circuitry, a processor, or the like, or a combination thereof. They may be formed of a single chip, or may be formed of a plurality of chips connected to each other through a bus. Some or all of the components of each apparatus may be implemented by a combination of the above-described circuit or the like and a program. Further, as the processor, a Central Processing Unit (CPU), a Graphics Processing Unit (GPU), a field-programmable gate array (FPGA), or the like may be used. Note that the above descriptions of the configurations may also be applied to other apparatuses or systems described below in the present disclosure.

Further, when some or all of the components of the image display apparatus 10 are implemented by a plurality of information processing apparatuses, circuits, or the like, the plurality of information processing apparatuses, circuits, or the like may be disposed in one place in a centralized manner or arranged in a discrete manner. For example, the information processing apparatuses, the circuits, or the like may be implemented as a form in which the information processing apparatuses, the circuits, or the like are connected to each other through a communication network, such as a client server system, a cloud computing system, or the like. Further, the functions of the image display apparatus 10 may be provided in the form of Software as a Service (SaaS).

The first example embodiment has been described above. The image display apparatus 10 according to the first example embodiment can detect a person of interest exhibiting a symptom of an infectious disease in a place where many people come and go, and further display an image including a situation in which an infectious disease may be transmitted to a person present in the vicinity of the person of interest. Therefore, according to the first example embodiment, it is possible to provide the image display apparatus and the like which suitably display a situation in which a risk of infection is high.

Second Example Embodiment

Figure 3:
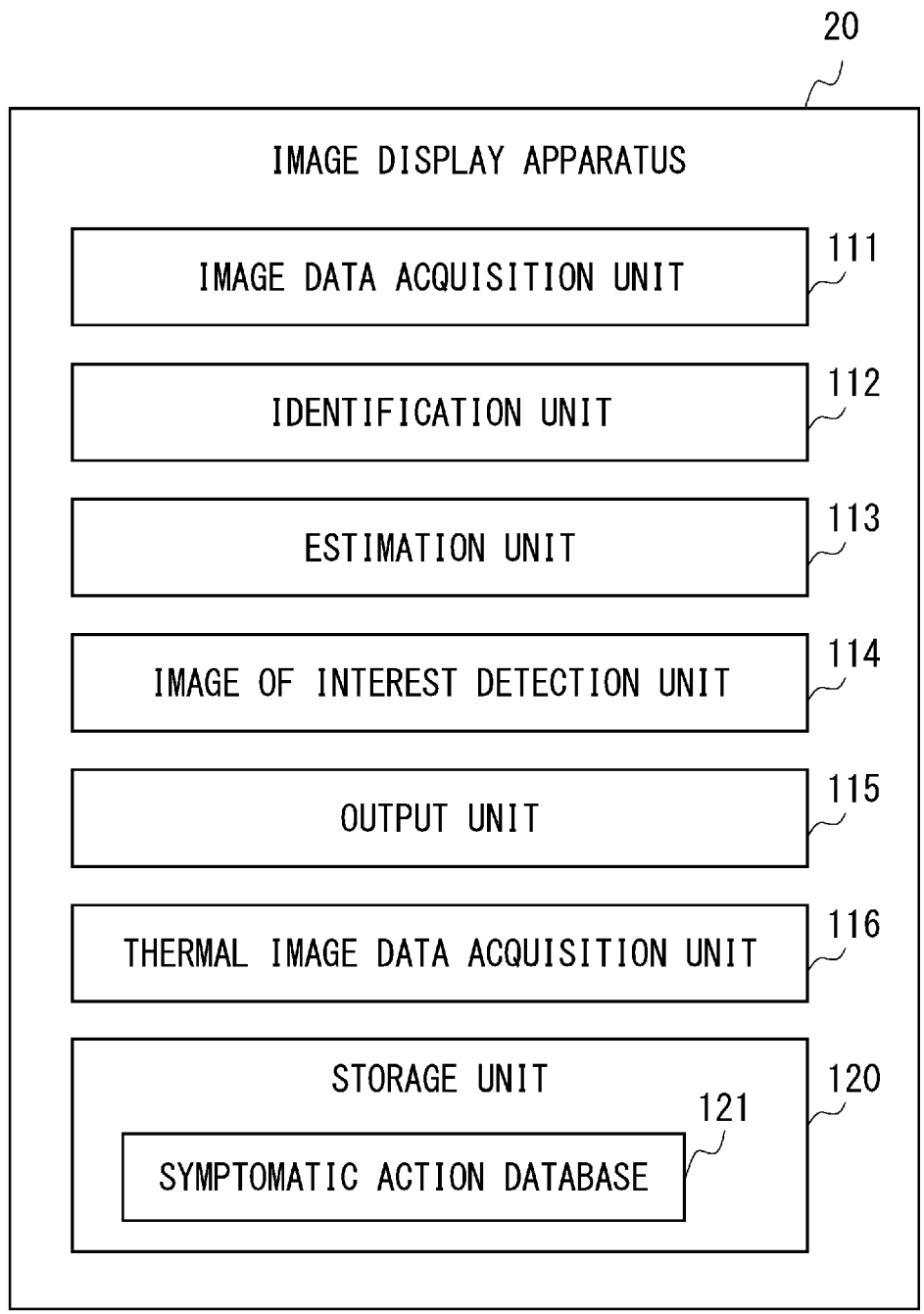
FIG. 3 is a block diagram of an image display apparatus according to a second example embodiment.

Next, a second example embodiment will be described. FIG. 3 is a block diagram of an image display apparatus 20 according to the second example embodiment. The image display apparatus 20 shown in FIG. 3 differs from the image display apparatus according to the first example embodiment in that it further includes a thermal image data acquisition unit 116 and a storage unit 120.

The thermal image data acquisition unit 116 acquires thermal image data from an infrared camera (or a thermal camera). Note that, in the following description, a camera connected to the image data acquisition unit 111 is also referred to as a "visible light camera" in order to make it easy to distinguish it from an infrared camera. Further, image data generated by a visible light camera is also referred to as "visible light image data". The infrared camera is installed so that it corresponds to the visible light camera connected to the image data acquisition unit 111.

The visible light camera and the infrared camera are installed in a predetermined facility, the vicinity of the facility, a predetermined place outdoors, or the like. The visible light camera captures scenery including a person, generates visible light image data of the captured image of the scenery, and supplies the generated visible light image data to the image data acquisition unit 111. The infrared camera captures scenery including a person, generates thermal image data of the captured image of the scenery, and supplies the generated thermal image data to the thermal image data acquisition unit 116.

The capturing range of the visible light camera and the capturing range of the infrared camera at least partially overlap each other. In other words, the capturing range of the infrared camera corresponds to at least part of a visible light image to be captured by the visible light camera. Further, it is preferable that the visible light camera and the infrared camera be fixed so that a positional relationship therebetween does not change. By the above configuration, the image capturing apparatus can associate an image of a person included in visible light image data generated by the visible light camera with an image of a person included in thermal image data generated by the infrared camera.

Note that one visible light camera and one infrared camera may be installed, or a plurality of each of these cameras may instead be installed. Further, for example, the visible light camera or the infrared camera may be movable so that a positional relationship therebetween changes. In this case, it is preferable that the visible light camera or the infrared camera temporarily pan, tilt, or zoom by, for example, a user's operation, and then automatically return to a predetermined position even when the angle of view has been changed.

The thermal image data acquisition unit 116 acquires thermal image data from the above-described infrared camera, and supplies the acquired thermal image data to the estimation unit 113.

The estimation unit 113 according to this example embodiment measures a body surface temperature of a person included in thermal image data. For example, the estimation unit 113 first extracts an image of a person from visible light image data. At this time, the estimation unit 113 may extract only an image of a specific part of the person's body, such as a face image. Next, the estimation unit 113 extracts thermal image data corresponding to the image of the identified person. Further, the estimation unit 113 measures a body surface temperature of the identified person from the extracted thermal image data. The estimation unit 113 may measure the body surface temperature from the part of the extracted thermal image data showing the highest temperature. Further, the estimation unit 113 may calculate a statistical value of the temperature of the extracted thermal image data and use the calculated statistical value as the body surface temperature of the person.

The estimation unit 113 estimates a possibility of the person having developed an infectious disease by using the body surface temperature of the person measured from the thermal image data. More specifically, for example, the estimation unit 113 measures the body surface temperature of the identified person and estimates that the identified person may possibly have developed an infectious disease when the measured value is greater than or equal to a preset threshold (e.g., 37.5° C.). Further, the estimation unit 113 may take into account the measured body surface temperature described above and symptomatic actions described below and then estimate a possibility of the identified person having developed an infectious disease.

Upon receiving the visible light image data, the estimation unit 113 detects an action state of the person from the image data of the person included in the received visible light image data. Then, the estimation unit 113 reads a symptomatic action database 121 stored in the storage unit 120. Further, the estimation unit 113 compares the action state of the detected person with a symptomatic action pattern included in the symptomatic action database 121, and determines whether or not the action state of the detected person matches the symptomatic action related to the development of an infectious disease. In this way, the estimation unit 113 estimates a possibility of the person having developed an infectious disease.

That is, the estimation unit 113 estimates that the person may possibly have developed an infectious disease when the action state of the person matches the symptomatic action related to the development of an infectious disease. More specifically, for example, the estimation unit 113 detects an action of coughing or sneezing done by the identified person from the image data. Meanwhile, the symptomatic action database 121 stores an action pattern of coughing or sneezing done by the person. When the estimation unit 113 compares the detected action with the symptomatic action pattern and determines they match each other, the estimation unit 113 estimates a possibility that the person who has done the detected action has developed an infectious disease. Note that, in the above description, a result of the comparison in which the detected action and the symptomatic action pattern match each other indicates that they substantially match each other, and the determination as to whether they match each other may be set as appropriate by a person skilled in the art.

The image of interest detection unit 114 according to this example embodiment detects that the person of interest and the nearby person are performing actions of interest. Note that, the "action of interest" is an action regarding a person including at least one of movement of the mouth of the person, putting on a mask, coughing, sneezing, and coming into contact with another person, and refers to a predetermined action by which it is determined the risk of infection with an infectious disease is increased. For example, when a person is actively moving the mouth of the person, it is assumed that the person is talking. When the image of interest detection unit 114 detects that, in an image including a person of interest and a nearby person, the person of interest and the nearby person are performing the above-described actions of interest, the image of interest detection unit 114 detects an image of interest.

The image of interest detection unit 114 may further take into account the degree of congestion of an area of an image of the image data including the person and then detect the image of interest. In this case, the image of interest detection unit 114 determines that the risk of infection with an infectious disease is relatively high when the degree of congestion is relatively high. The image of interest detection unit 114 may calculate a predetermined population density from the relationship between the space and the number of people in the image data as the degree of congestion. Further, the image of interest detection unit 114 may detect, as the degree of congestion, a crowd in the image data. A crowd indicates a state in which it appears that a plurality of people overlap each other in a predetermined space. In this case, the image of interest detection unit 114 may detect the crowd, specify a congestion state of the detected crowd, and then calculate the degree of congestion.

Note that, when the person of interest and the nearby person are continuously present in the same angle of view, the image of interest detection unit 114 may be configured to detect one image of interest from the images captured during a period in which the person of interest and the nearby person are present. By doing so, the image of interest detection unit 114 can prevent a redundant detection of an image of interest.

The storage unit 120 is a storage device including a non-volatile memory such as an Erasable Programmable Read Only Memory (EPROM) or a flash memory. The storage unit 120 stores the symptomatic action database 121. The symptomatic action database 121 is a database for estimating a possibility of a person having developed an infectious disease and includes symptomatic action patterns of a person who has developed an infectious disease. As described above, the storage unit 120 supplies the symptomatic action database 121 as appropriate to the estimation unit 113. The symptomatic action database 121 may include a plurality of symptomatic action patterns. Further, the data included in the symptomatic action database 121 may be updated as appropriate.

Figure 4:
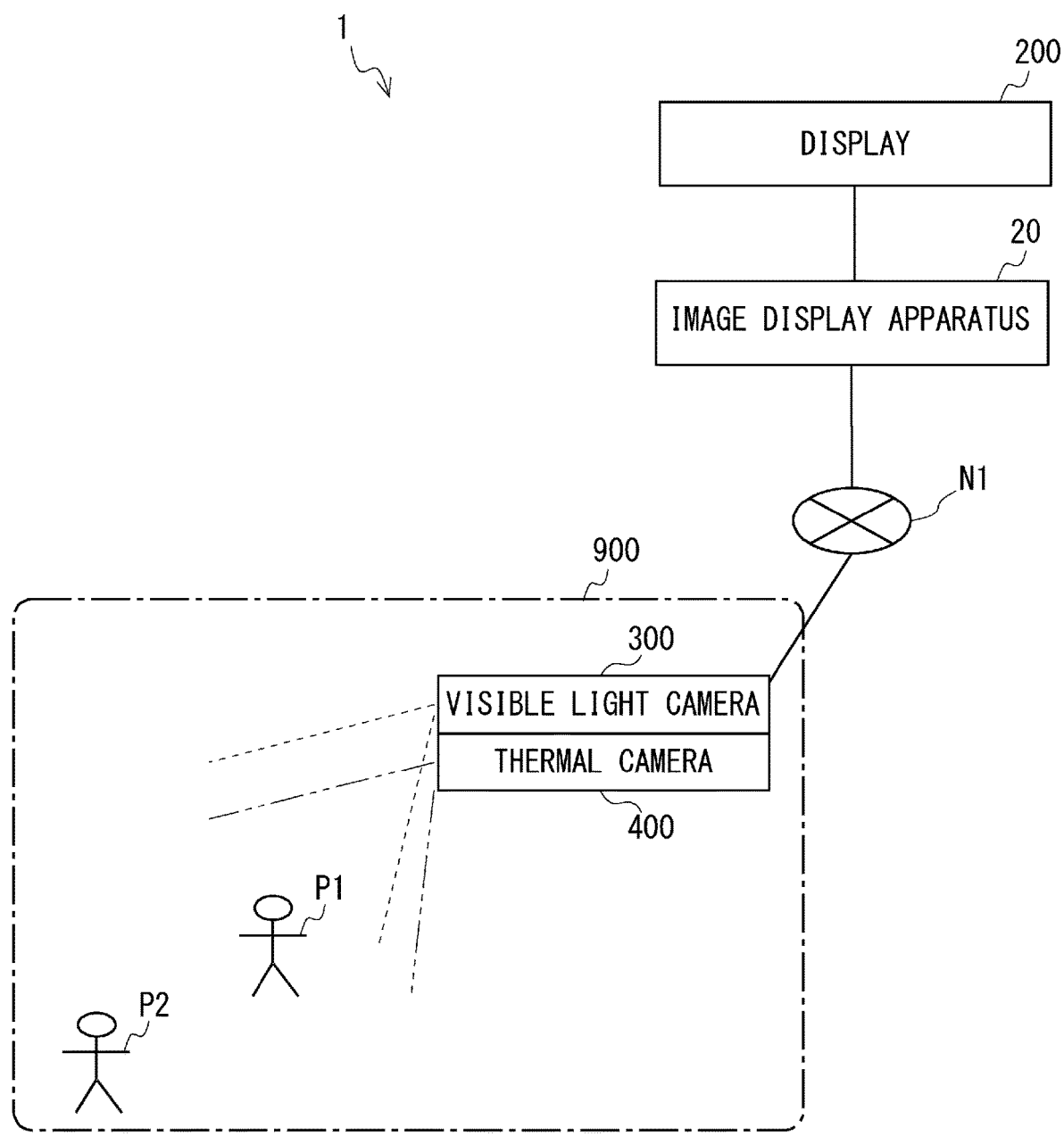
FIG. 4 is a block diagram of an image display system according to the second example embodiment.

Next, a configuration of a system including the image display apparatus 20 will be described with reference to FIG. 4. FIG. 4 is a block diagram of an image display system 1 according to the second example embodiment. The image display system 1 is installed for the purpose of knowing the risk of people being infected with an infectious disease in a facility 900. The image display system 1 mainly includes the image display apparatus 20, an image display apparatus, a visible light camera 300, and a thermal camera 400.

The visible light camera 300 and the thermal camera 400 are fixed at a predetermined position in the facility 900 and captures people in the facility 900. The visible light camera 300 and the thermal camera 400 are connected to the image display apparatus 20 through a network N1, which is a communication network, so that they can communicate with the image display apparatus 20. As shown in FIG. 4, for example, the visible light camera 300 captures a person P1 and a person P2 at an angle of view indicated by a dotted line, generates visible light image data, and supplies it to the image display apparatus 20. Further, the thermal camera 400 captures the persons P1 and P2 at an angle of view indicated by an alternate long and two short dashes line, generates thermal image data, and supplies it to the image display apparatus 20.

The image display apparatus 20 shown in FIG. 4 is connected to the visible light camera 300 through the network N1, and receives visible light image data. Further, the image display apparatus 20 is connected to the thermal camera 400 through the network N1, and receives thermal image data. Further, the image display apparatus 20 is connected to a display 200 so that it can communicate with the display 200, and outputs image data of a series of images through the output unit 115. Note that, in the example shown in FIG. 4, although one visible light camera 300 and one thermal camera 400 are shown, a plurality of each of these cameras may be installed. A plurality of cameras capture different places and supply image data respectively captured by the cameras to the image display apparatus 20, whereby the image display system 1 can know the risk of infection in a wide area of the facility 900.

The display 200 is a display apparatus including, for example, a liquid crystal display and an organic electroluminescence. The display 200 is connected to the image display apparatus 20 so that it can communicate with the image display apparatus 20, and receives image data from the image display apparatus 20 and displays the received image data. Note that, in the example shown in FIG. 4, although the image display apparatus 20 and the display 200 are connected to each other without using the network N1, they may instead be connected to each other through the network N1. A user of the image display system 1 visually recognizes a group of images displayed on the display 200, whereby the user can know the contact state between the person of interest, who is likely to be an infected person, and the nearby person.

Figure 5:
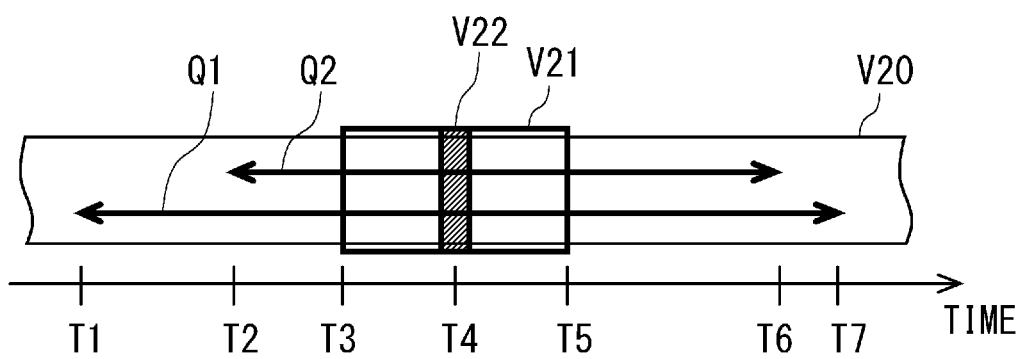
FIG. 5 is a diagram showing an example of a group of images extracted by the image display apparatus according to the second example embodiment.

Next, a group of images extracted by the image display apparatus 20 will be described with reference to FIG. 5. FIG. 5 is a diagram showing an example of the group of images extracted by the image display apparatus according to the second example embodiment. In FIG. 5, an arrow extending horizontally from the left to the right indicates the passage of time. Further, in FIG. 5, a band shape extending parallel to the arrow and indicating a capturing period V20 is shown above the arrow. The capturing period V20 schematically indicates a period during which a plurality of images, i.e., a moving image, captured by the visible light camera 300 are continuously generated.

A first period Q1 and a second period Q2 extending in the left and right directions are shown in the capturing period V20. The first period Q1 indicates a period during which the person P1 is included in an image which the visible light camera 300 is capturing. The second period Q2 indicates a period during which the person P2 is included in an image which the visible light camera 300 is capturing. Specifically, the first period Q1 indicates a period from a time T1 to a time T7. The second period Q2 indicates a period from the time T2, which is the time after the time T1, to the time T6, which is the time before the time T7.

An extraction period V21 shown by a thick-line frame is superimposed on a central part of the band shape V20. The extraction period V21, which is a period during which the person P1 is approaching the person P2, indicates a period during which a series of images extracted by the output unit 115 have been captured. More specifically, the extraction period V21 indicates a period from the time T3, which is the time after the time T3, to the time T5, which the time before the time T6. A time of interest V22 indicated by hatching is shown in the central part of the extraction period V21. The time of interest V22 is the time T4, which is the time after the time T3 and before the time T5.

In FIG. 5, the time T4 is the time at which the image of interest detected by the image of interest detection unit 114 has been captured. That is, at the time T4, for example, the person P1 and the person P2 are the closest to each other and thus it has been determined that the risk of infection is high. Therefore, the image of interest detection unit 114 has detected the image captured at the time T4 as the image of interest. Further, the output unit 115 extracts images captured during a preset period (i.e., from the time T3 to the time T5) before and after the time when the image of interest has been captured as a series of images.

A group of images extracted by the image display apparatus 20 has been described above. Note that the above-described method by which the output unit 115 extracts a group of images is merely an example, and a method by which the output unit 115 extracts a group of images is not limited to the above-described method. For example, the output unit 115 may extract images captured during a period in which the person P2 is included in the angle of view, that is, a period from the time T2 to the time T6. Further, the output unit 115 may extract images captured during a period in which the person P1 is included in the angle of view, that is, a period from the time T1 to the time T7. Note that, when the output unit 115 extracts a series of images, the output unit 115 may change the frame rate and the image quality of image data.

The second example embodiment has been described above. The image display apparatus 20 and the image display system 1 according to the second example embodiment can detect a person of interest exhibiting a symptom of an infectious disease in a place where many people come and go, and further display an image including a situation in which an infectious disease may be transmitted to a person present in the vicinity of the person of interest. Therefore, according to the second example embodiment, it is possible to provide the image display apparatus, the image display system, and the like which suitably display a situation in which a risk of infection is high.

Third Example Embodiment

Figure 6:
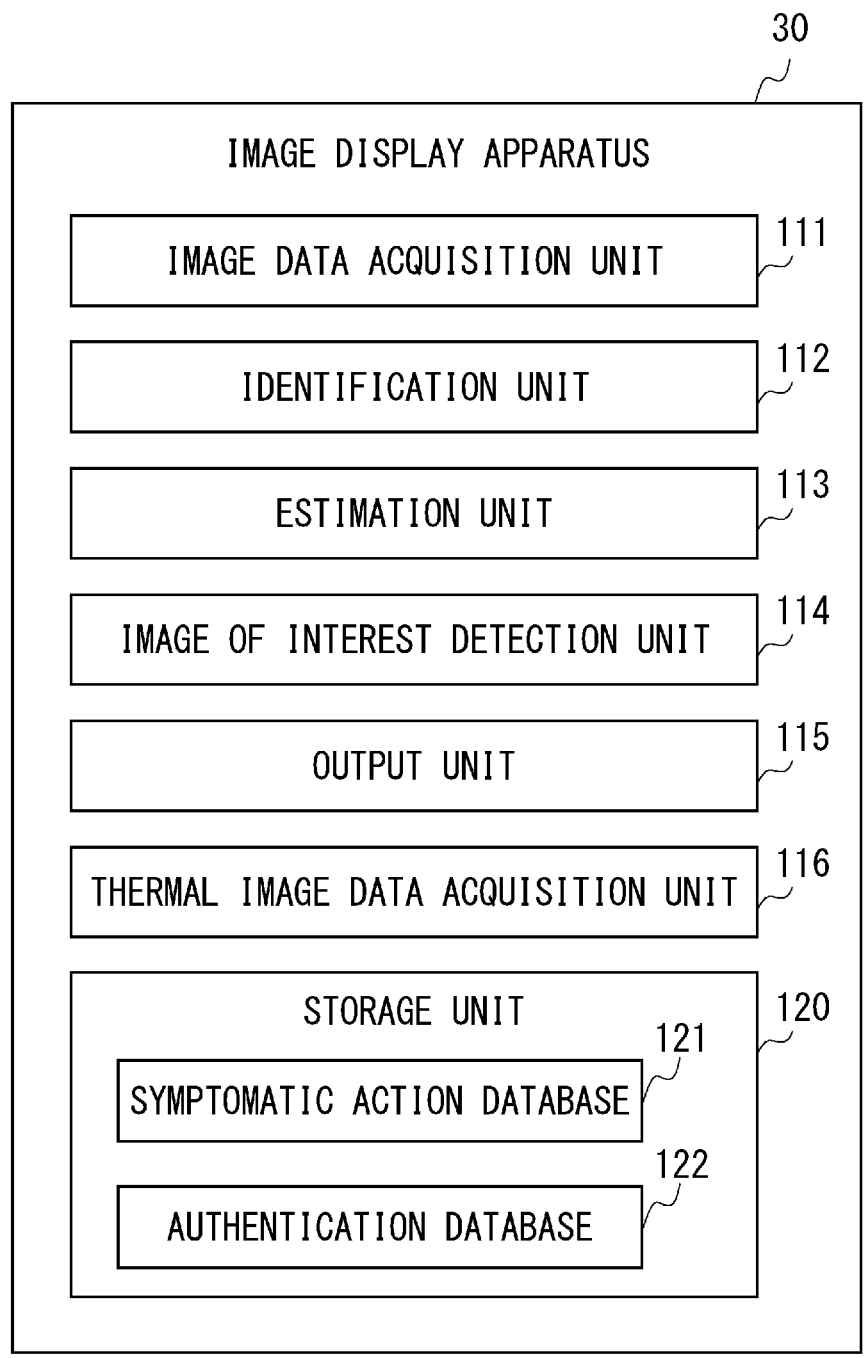
FIG. 6 is a block diagram of an image display apparatus according to a third example embodiment.

Next, a third example embodiment will be described. FIG. 6 is a block diagram of an image display apparatus 30 according to the third example embodiment. The image display apparatus 30 shown in FIG. 6 differs from the image display apparatuses according to the above-described example embodiments in that the storage unit 120 stores an authentication database. Further, the image display apparatus 30 shown in FIG. 6 differs from the image display apparatuses according to the above-described example embodiments in processing performed by the identification unit 112.

An authentication database 122 includes authentication data of a person and attribute data of a person. The authentication data is data used for authentication performed by the identification unit 112. The authentication data is data for identifying features unique to a person, such as feature data of a face image. The authentication data may be iris data or ear shape data.

The attribute data is data associated with a person subjected to authentication, and is used to determine the risk of infection with an infectious disease. For example, the attribute data may include antibody certificate data which a person subjected to authentication has. The antibody certificate data is data indicating whether or not a person has antibodies for an infectious disease. Further, the attribute data may be the past medical history of a person subjected to authentication related to an infectious disease the person has been infected with or other information about a person subjected to authentication related to the resistance of the person to an infectious disease.

The identification unit 112 according to this example embodiment authenticates a person by using authentication data in addition to identifying the person. When the identification unit 112 identifies a person, the identification unit 112 uses authentication data included in the authentication database 122. The identification unit 112 supplies a result of the authentication to the estimation unit 113. The estimation unit 113 estimates a possibility of a person subjected to authentication being infected from the data received from the identification unit 112.

Specifically, for example, when the body surface temperature of a person subjected to authentication is greater than or equal to a threshold or when a person subjected to authentication performs an action that match a symptomatic action pattern and this person has an antibody certificate, the estimation unit 113 determines whether or not the person is exhibiting a symptom after the aforementioned facts are taken into account. That is, when the body surface temperature of a person who has an antibody certificate is greater than or equal to a threshold or when a person who has an antibody certificate performs an action that match a symptomatic action pattern, the estimation unit 113 may not determine that the person may be exhibiting a symptom of an infectious disease.

Further, the image of interest detection unit 114 according to this example embodiment detects an image of interest based on attribute data. For example, the image of interest detection unit 114 takes into account antibody certificate data of a person subjected to authentication and then detects the image of interest. More specifically, when a nearby person present near the person of interest has an antibody certificate, the image of interest detection unit 114 does not determine that the possibility of this nearby person being infected is high. Therefore, even when a person who has an antibody certificate is present near the person of interest, the image of interest detection unit 114 may not detect the image captured under such a situation as the image of interest.

The third example embodiment has been described above. The image display apparatus 30 according to the third example embodiment can detect a person of interest exhibiting a symptom of an infectious disease in a place where many people come and go, and further display an image including a situation in which an infectious disease may be transmitted to a person present in the vicinity of the person of interest. Further, when the image display apparatus 30 detects a person of interest or extracts an image of interest, the image display apparatus 30 performs the processing after attribute data of a person subjected to authentication is taken into account. Therefore, according to the third example embodiment, it is possible to provide the image display apparatus and the like which suitably display a situation in which a risk of infection is high after individual circumstances of people are taken into account.

Fourth Example Embodiment

Figure 7:
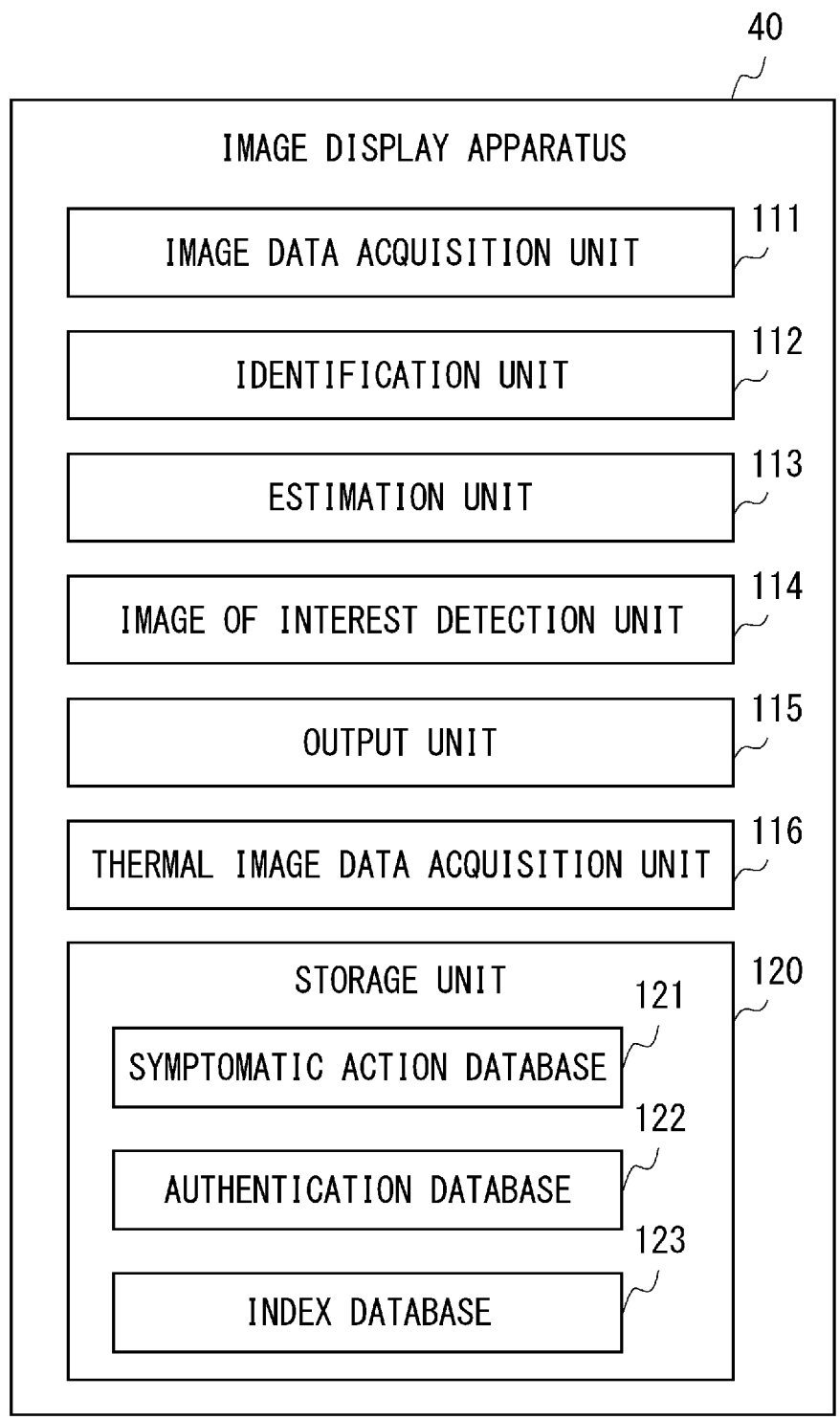
FIG. 7 is a block diagram of an image display apparatus according to a fourth example embodiment.

Next, a fourth example embodiment will be described. An image display apparatus 40 according to the fourth example embodiment differs from the image display apparatuses according to the above-described example embodiments in that the storage unit 120 stores an index database 123, and the image of interest detection unit 114 uses the index database 123. FIG. 7 is a block diagram of the image display apparatus 40 according to the fourth example embodiment.

The image of interest detection unit 114 according to this example embodiment takes into account an infection risk index related to a capturing place of image data to be acquired (i.e., a place where image data to be acquired has been captured) and then detects an image of interest. For example, when there are an image in which a person of interest comes into contact with a nearby person in a place where the infection index is relatively high and an image in which a person of interest comes into contact with a nearby person in a place where the infection index is relatively low, the image of interest detection unit 114 detects the former image as an image of interest and may not detect the latter image.

The storage unit 120 according to this example embodiment stores the index database 123. The index database 123 is a database including an infection risk index related to a capturing place of image data to be acquired. The index database 123 is associated with a camera that captures a predetermined capturing place and includes preset values.

For example, an infection risk index associated with outdoor image data is set lower than an infection risk index associated with indoor image data. Further, even when image data is indoor image data, an infection risk index associated with image data of a relatively small space is set higher than an infection risk index associated with image data of a relatively large space. Further, in accordance with, for example, the ventilation condition of a room and the shape of a room, an infection risk index may be set higher in a place where the air flow is not relatively good than in a place where the air flow is relatively good. Note that different infection risk indices may be set for different capturing areas in image data captured by one camera.

Further, the infection risk index may be updated as appropriate. For example, when a person of interest has stayed in the same place for a period longer than a preset period, the image of interest detection unit 114 may temporarily set the infection risk index of the place where the person of interest has stayed high. In this case, the image of interest detection unit 114 may detect an area of interest where the person of interest has stayed for a period longer than a preset period, and detect an image in which the nearby person is present in the area of interest as an image of interest.

The fourth example embodiment has been described above. When the image display apparatus 40 extracts an image of interest, the image display apparatus 40 takes into account the infection risk index of a capturing place and then performs the processing. Therefore, according to the fourth example embodiment, it is possible to provide the image display apparatus and the like which suitably display a situation in which a risk of infection is high after circumstances of the capturing place are taken into account.

Fifth Example Embodiment

Figure 8:
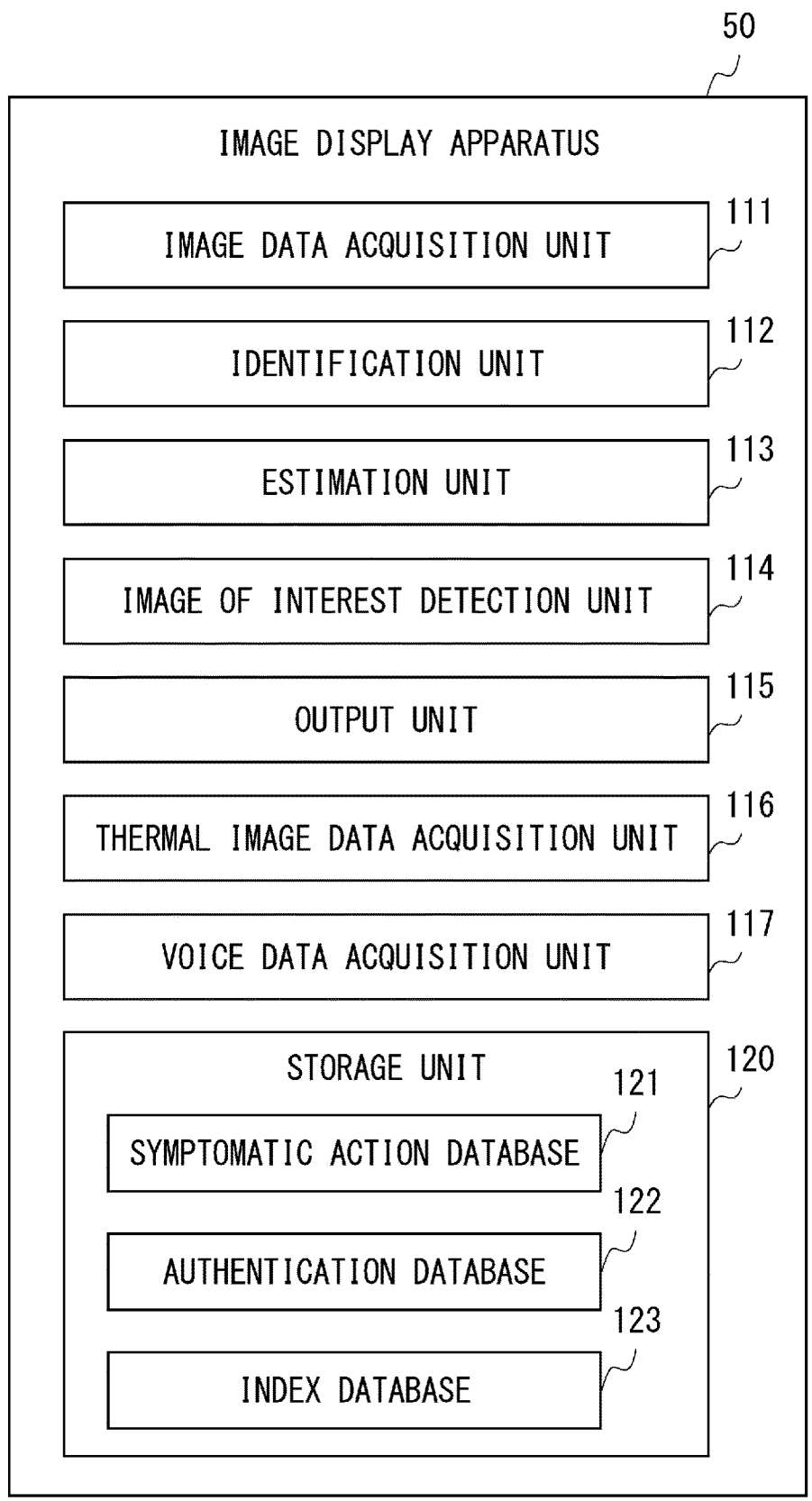
FIG. 8 is a block diagram of an image display apparatus according to a fifth example embodiment.

Next, a fifth example embodiment will be described. An image display apparatus according to the fifth example embodiment differs from the image display apparatuses according to the above-described example embodiments in that it further includes a voice data acquisition unit and that voice data is used when a person of interest and an image of interest are detected. FIG. 8 is a block diagram of an image display apparatus 50 according to the fifth example embodiment.

The image display apparatus 50 includes a voice data acquisition unit 117. The voice data acquisition unit 117 acquires voice data generated by sounds collected by a microphone installed in the capturing area of image data. The voice data acquisition unit 117 supplies the acquired voice data to the estimation unit 113 and the image of interest detection unit 114.

The estimation unit 113 according to this example embodiment estimates a possibility of an identified person developing an infectious disease from a voice uttered by the identified person. For example, the estimation unit 113 extracts a voice which it is estimated is uttered by the identified person from the voice data received from the voice data acquisition unit 117. At this time, the estimation unit 113 may analyze visible light image data or thermal image data in addition to the voice data. When the identified person is coughing, sneezing, etc., the estimation unit 113 associates these actions with the symptomatic action pattern.

Further, the image of interest detection unit 114 according to this example embodiment receives voice data from the voice data acquisition unit 117, and detects a voice uttered by the person of interest and the nearby person from the received voice data. Then, the image of interest detection unit 114 detects that the person of interest is coughing or sneezing near the nearby person, that the person of interest is talking to the nearby person, that the person of interest is shouting, or the like. In this case, the image of interest detection unit 114 may detect the aforementioned voice after it analyzes the body posture of the person of interest and the body posture of the nearby person in the visible light image data or the thermal image data together. By the above method, the image of interest detection unit 114 detects an image of interest from image data.

The fifth example embodiment has been described above. The image display apparatus 50 uses voice data when it determines a person of interest or detects an image of interest. By doing so, the accuracy of the image display apparatus 50 for displaying a desired image is increased. Therefore, according to the fifth example embodiment, it is possible to provide the image display apparatus and the like which accurately display a situation in which a risk of infection is high.

Sixth Example Embodiment

Figure 9:
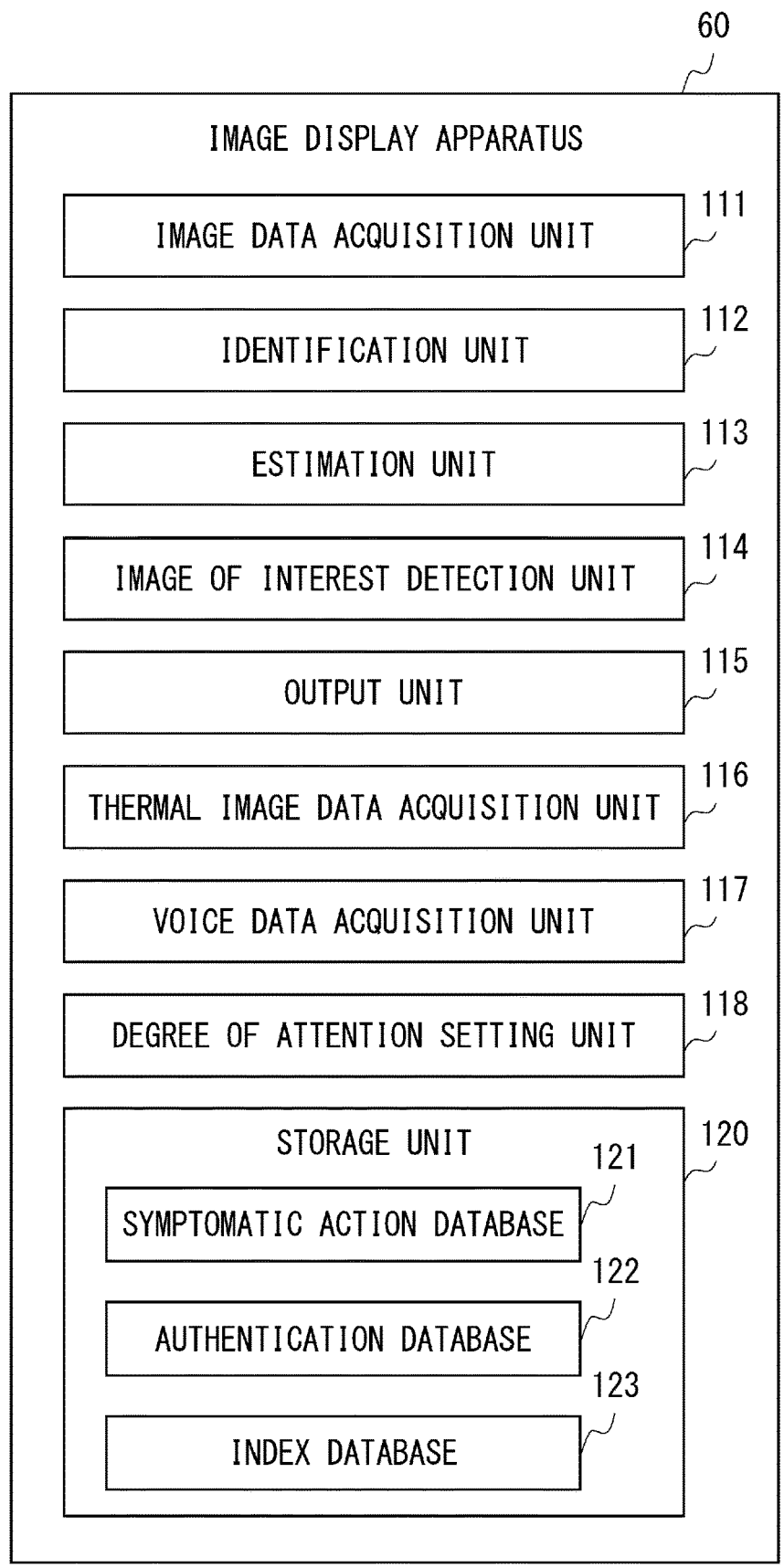
FIG. 9 is a block diagram of an image display apparatus according to a sixth example embodiment.

Next, a sixth example embodiment will be described. The sixth example embodiment differs from the above-described example embodiments in that a degree of attention setting unit is included. FIG. 9 is a block diagram of an image display apparatus 60 according to the sixth example embodiment. The image display apparatus 60 includes a degree of attention setting unit 118.

The degree of attention setting unit 118 sets a degree of attention in an image of interest. The degree of attention is an index for displaying a series of images, and can also be referred to as a display priority. The degree of attention is indicated, for example, by a numerical value within a predetermined range. The predetermined range may be a range of several levels, for example, 0, 1, and 2. For example, a group of images having a higher degree of attention indicates a situation in which it is more likely that an infectious disease has been transmitted to a nearby person. The degree of attention setting unit 118 analyzes the contact state between the person of interest and the nearby person and sets the degree of attention in accordance with a result of the analysis. Specifically, for example, the degree of attention setting unit 118 sets a degree of attention (a first degree of attention) of an image in which the person of interest and the nearby person face each other at close range and are having a conversation higher than a degree of attention (a second degree of attention) of an image in which the person of interest and the nearby person are not having a conversation.

Further, in addition to the example described above, for example, the degree of attention setting unit 118 sets the degree of attention higher when the person of interest is facing the nearby person in a situation in which a large number of people are present and it is thus crowded than when the person of interest is facing the nearby person in a situation in which it is not crowded. Alternatively, when the person of interest is facing the nearby person and the person of interest and the nearby person are not putting on masks, the degree of attention setting unit 118 sets the degree of attention higher than that when they are putting on masks. Alternatively, when the person of interest is facing the nearby person and the infection risk index of the place where the person of interest is facing the nearby person is high, the degree of attention setting unit 118 sets the degree of attention higher than that in a similar situation where the infection risk index is low.

In this case, the output unit 115 sets a display priority in such a manner that the higher the degree of attention of a group of images, the higher the display priority of the group of images becomes, and outputs the group of images. That is, the output unit 115 outputs the group of images set to be the first degree of attention, which is a relatively high degree of attention, in preference to the group of images set to be the second degree of attention, which is a relatively low degree of attention.

Figure 10:
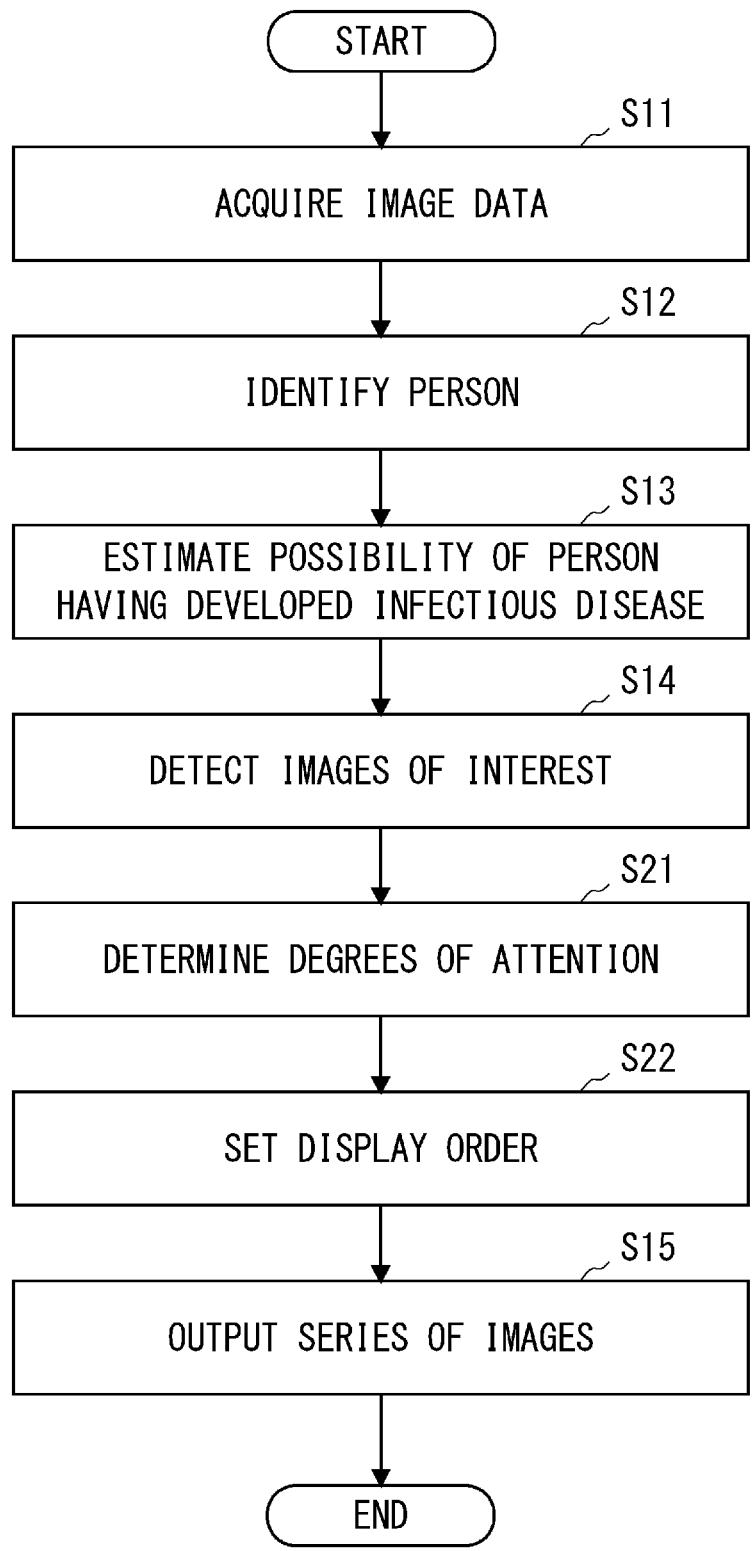
FIG. 10 is a flowchart showing an image display method according to the sixth example embodiment.

Next, processing performed by the image display apparatus 60 will be described with reference to FIG. 10. FIG. 10 is a flowchart showing an image display method according to the sixth example embodiment. The flowchart shown in FIG. 10 differs from the flowchart shown in FIG. 2 in that Steps S21 and S22 are added between Steps S14 and S15.

In Step S14, the image of interest detection unit 114 detects, from the result of the estimation received from the estimation unit 113, images of interest including the person of interest regarding which there is a possibility of the person of interest having developed an infectious disease and a nearby person present in the vicinity of the person of interest (Step S14). The image of interest detection unit 114 supplies the detected images of interest to the output unit 115 and the degree of attention setting unit 118.

Next, the degree of attention setting unit 118 sets degrees of attention in the images of interest received from the image of interest detection unit 114 (Step S21). The degree of attention setting unit 118 supplies the degrees of attention set in the images of interest to the output unit 115.

Next, the output unit 115 sets a display order of the images of interest in accordance with the set degrees of attention (Step S22).

Next, the output unit 115 extracts a series of images including the image of interest from the images of interest received from the image of interest detection unit 114, and outputs the extracted series of images to the display apparatus in accordance with the aforementioned display order (Step S15).

The processing performed by the image display apparatus 60 has been described above. When the image display apparatus 60 detects a plurality of images of interest and extracts a plurality of groups of images accordingly, it outputs them in a descending order of the degrees of attention. By setting the degree of attention in this way, the image display apparatus 60 can quickly show a situation in which a risk of infection is high to a user. Note that, although the output unit 115 outputs a plurality of groups of images in accordance with the display order set in accordance with the degrees of attention, the output processing may be performed sequentially in response to a user's operation.

Figure 11:
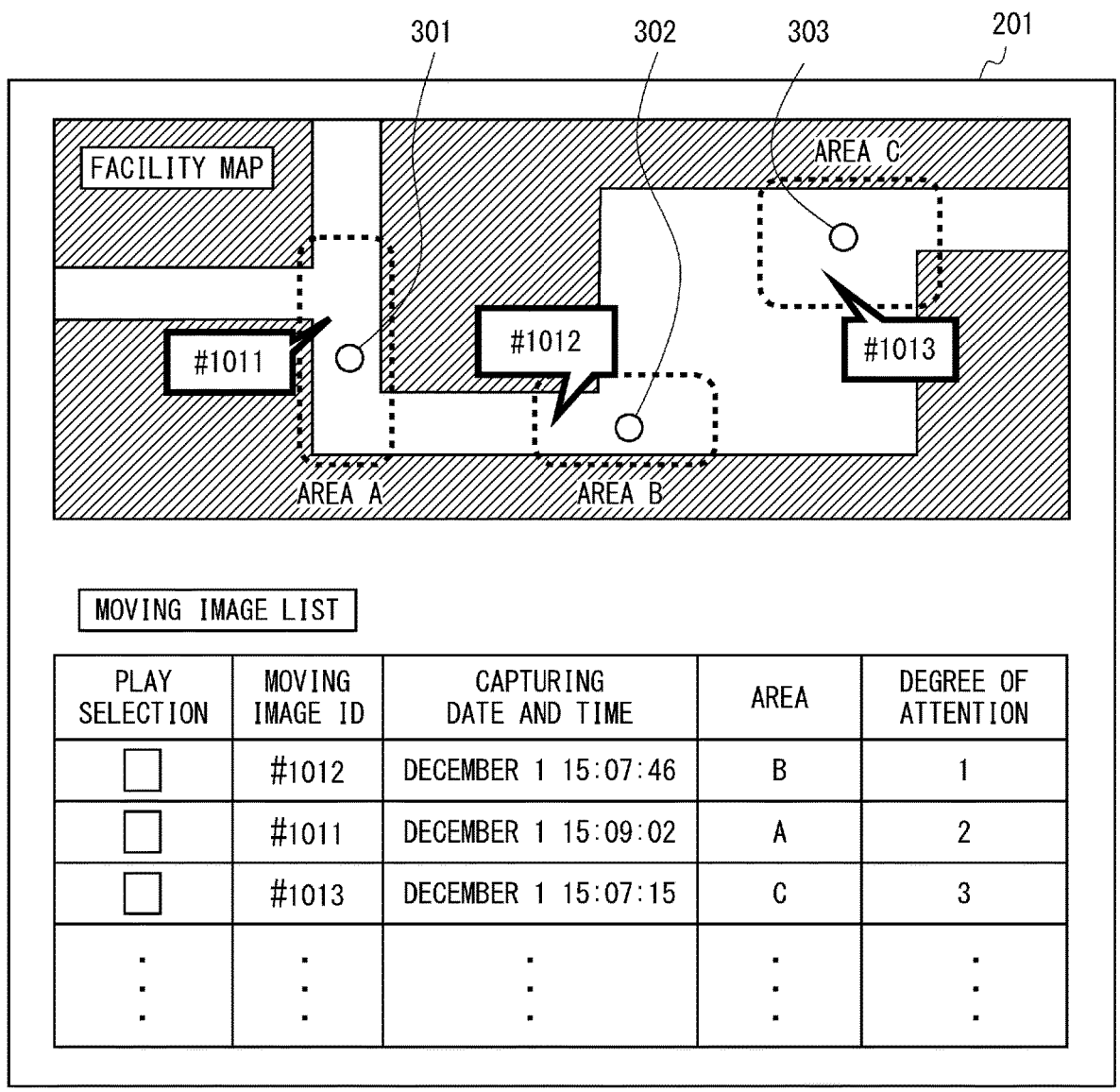
FIG. 11 is a diagram showing an example of an image displayed by the image display apparatus according to the sixth example embodiment.

Next, an example of an image displayed by the image display apparatus 60 will be described with reference to FIG. 11. FIG. 11 is a diagram showing the example of an image displayed by the image display apparatus 60 according to the sixth example embodiment.

FIG. 11 shows an image 201 displayed by the display apparatus. In the upper part of the image 201, a facility map is shown. The facility map shows positions where cameras 301, 302, and 303 are respectively installed, and shows areas A, B, and C as capturing ranges of the respective cameras. Further, an icon with ID #1011 is shown in the area A. This icon indicates that a group of images of ID #1011 has been extracted in the area A. Similarly, an icon with ID #1012 is shown in the area B. This icon indicates that a group of images of ID #1012 has been extracted in the area B. An icon with ID #1013 is shown in the area C. This icon indicates that a group of images of ID #1013 has been extracted in the area C. A user who visually recognizes the image 201 selects the icons shown on the facility map, whereby it is possible to play the moving images corresponding to the icons.

In the lower part of the image 201, a moving image list is shown. The moving image IDs of #1011, #1012, and #1013 are listed in the moving image list. The capturing day, the capturing area, and the degree of attention corresponding to each of the moving images are also listed. In FIG. 11, the moving image ID of #1012 corresponding to the degree of attention "1" has the highest degree of attention. Further, the moving image ID of #1011 corresponding to the degree of attention "2" has the second highest degree of attention. Further, the moving image ID of #1013 corresponding to the degree of attention "3" has the third highest degree of attention. A user who visually recognizes the image 201 can play the moving images in the order of the degrees of attention. Further, a user can also play the selected moving image regardless of the degree of attention.

The sixth example embodiment has been described above. The image display apparatus 60 can suitably output a desired group of images by setting the degree of attention. Therefore, according to the sixth example embodiment, it is possible to provide the image display apparatus and the like which efficiently display a situation in which a risk of infection is high.

Note that the above-described program can be stored and provided to a computer using any type of non-transitory computer readable media. Non-transitory computer readable media include any type of tangible storage media. Examples of non-transitory computer readable media include magnetic storage media (e.g., floppy disks, magnetic tapes, and hard disk drives), optical magnetic storage media (e.g., magneto-optical disks), CD-Read Only Memory (ROM), CD-R, CD-R/W, semiconductor memories (e.g., mask ROM, Programmable ROM (PROM), Erasable PROM (EPROM), flash ROM, and Random Access Memory (RAM)). Further, the program may be provided to a computer using any type of transitory computer readable media. Examples of transitory computer readable media include electric signals, optical signals, and electromagnetic waves. Transitory computer readable media can provide the program to a computer via a wired communication line (e.g., electric wires and optical fibers) or a wireless communication line.

Note that the present invention is not limited to the above-described example embodiments and may be changed as appropriate without departing from the scope and spirit of the present invention.

The whole or part of the example embodiments disclosed above can be described as, but not limited to, the following supplementary notes.

(Supplementary Note 1)

An image display apparatus comprising:
  image data acquisition means for acquiring a plurality of pieces of image data from a camera;
  identification means for identifying a person from the image data;
  estimation means for estimating a possibility of the person identified from the image data having developed an infectious disease;
  image of interest detection means for detecting an image of interest including a person of interest regarding which there is the possibility of the person of interest having developed an infectious disease and a nearby person present in the vicinity of the person of interest based on a result of the estimation; and output means for extracting a series of images including the image of interest and displaying the extracted series of images.

(Supplementary Note 2)

The image display apparatus according to Supplementary note 1, further comprising thermal image data acquisition means for acquiring thermal image data from an infrared camera, wherein the estimation means estimates the possibility of the person having developed an infectious disease based on a body surface temperature of the person measured from the thermal image data corresponding to the image data.

(Supplementary Note 3)

The image display apparatus according to Supplementary note 1 or 2, further comprising symptomatic action storage means for storing a symptomatic action that is done when an infectious disease has been developed, wherein the estimation means detects an action done by the identified person, and determines whether or not the detected action matches the symptomatic action, thereby estimating the possibility of the person having developed an infectious disease.

(Supplementary Note 4)

The image display apparatus according to Supplementary note 3, wherein the symptomatic action storage means stores an action of coughing or an action of sneezing of the person as the symptomatic action, and the estimation means detects the action of coughing or the action of sneezing of the person.

(Supplementary Note 5)

The image display apparatus according to any one of Supplementary notes 1 to 4, wherein the image of interest detection means detects, as the image of interest, an image in which the person of interest and the nearby person are present at a distance less than a threshold from each other for a predetermined period or longer.

(Supplementary Note 6)

The image display apparatus according to any one of Supplementary notes 1 to 5, wherein the image of interest detection means detects an action of interest regarding the person of interest and the nearby person, the action of interest including at least one of movement of the mouth of the person, putting on a mask, coughing, sneezing, and coming into contact with each other, and detects the image of interest based on the action of interest.

(Supplementary Note 7)

The image display apparatus according to any one of Supplementary notes 1 to 6, wherein the image of interest detection means further takes into account a degree of congestion of an area of an image of the image data including the person and then detects the image of interest.

(Supplementary Note 8)

The image display apparatus according to any one of Supplementary notes 1 to 7, further comprising authentication data storage means for storing authentication data of the person and attribute data of the person, wherein the identification means, in addition to identifying the person, authenticates the person based on the authentication data, and the image of interest detection means detects the image of interest based on the attribute data.

(Supplementary Note 9)

The image display apparatus according to Supplementary note 8, wherein the authentication data storage means includes, in the attribute data, antibody certificate data which the person has, and the image of interest detection means takes into account the antibody certificate data of the person subjected to the authentication and then detects the image of interest.

(Supplementary Note 10)

The image display apparatus according to any one of Supplementary notes 1 to 9, further comprising index storage means for storing an infection risk index related to a capturing place of the image data to be acquired, wherein the image of interest detection means takes into account the infection risk index related to the capturing place of the image data to be acquired and then detects the image of interest.

(Supplementary Note 11)

The image display apparatus according to any one of Supplementary notes 1 to 10, wherein the image of interest detection means detects an area of interest where the person of interest has stayed for a period longer than a preset period, and detects an image in which the nearby person is present in the area of interest as the image of interest.

(Supplementary Note 12)

The image display apparatus according to any one of Supplementary notes 1 to 11, further comprising voice data acquisition means for acquiring voice data in a capturing area of the image data, wherein the estimation means estimates the possibility of the person having developed an infectious disease based on a voice uttered by the person.

(Supplementary Note 13)

The image display apparatus according to any one of Supplementary notes 1 to 12, wherein the image of interest detection means detects the image of interest based on voices uttered by the person of interest and the nearby person.

(Supplementary Note 14)

The image display apparatus according to any one of Supplementary notes 1 to 13, further comprising degree of attention setting means for setting a degree of attention in the image of interest based on a contact state between the person of interest and the nearby person, wherein the output means outputs a series of images based on the degree of attention.

(Supplementary Note 15)

The image display apparatus according to any one of Supplementary notes 1 to 13, further comprising degree of attention setting means for estimating a risk of the nearby person being infected and setting a degree of attention in the image of interest based on the risk of the nearby person being infected, wherein the output means outputs a series of images based on the degree of attention.

(Supplementary Note 16)

The image display apparatus according to Supplementary note 14 or 15, wherein the degree of attention setting means sets a priority of the series of images to be displayed so that it becomes higher as the degree of attention becomes higher, and the output means outputs the series of images set to be a first degree of attention in preference to the series of images set to be a second degree of attention, the first degree of attention being a relatively high degree of attention and the second degree of attention being a relatively low degree of attention.

(Supplementary Note 17)
An image display system comprising:
the image display apparatus according to any one of Supplementary notes 1 to 16; and
at least one of a camera configured to supply the image data to the image data acquisition means and a display apparatus configured to receive the series of images from the output means and display the received series of images.

(Supplementary Note 18)
An image display method executed by a computer, the image display method comprising:
acquiring a plurality of pieces of image data from a camera;
identifying a person from the image data;
estimating a possibility of the identified person having developed an infectious disease;
detecting an image of interest including a person of interest regarding which there is the possibility of the person of interest having developed an infectious disease and a nearby person present in the vicinity of the person of interest based on a result of the estimation; and
extracting a series of images including the image of interest and displaying the extracted series of images.

(Supplementary Note 19)
A non-transitory computer readable medium storing a program for causing a computer to:
acquire a plurality of pieces of image data from a camera;
identify a person from the image data;
estimate a possibility of the identified person having developed an infectious disease;
detect an image of interest including a person of interest regarding which there is the possibility of the person of interest having developed an infectious disease and a nearby person present in the vicinity of the person of interest based on a result of the estimation; and
extract a series of images including the image of interest and display the extracted series of images.

This application is based upon and claims the benefit of priority from Japanese patent application No. 2020-206504, filed on Dec. 14, 2020, the disclosure of which is incorporated herein in its entirety by reference.

REFERENCE SIGNS LIST

1 IMAGE DISPLAY SYSTEM
10 IMAGE DISPLAY APPARATUS
20 IMAGE DISPLAY APPARATUS
30 IMAGE DISPLAY APPARATUS
40 IMAGE DISPLAY APPARATUS
50 IMAGE DISPLAY APPARATUS
60 IMAGE DISPLAY APPARATUS
111 IMAGE DATA ACQUISITION UNIT
112 IDENTIFICATION UNIT
113 ESTIMATION UNIT
114 IMAGE OF INTEREST DETECTION UNIT
115 OUTPUT UNIT
116 THERMAL IMAGE DATA ACQUISITION UNIT
117 VOICE DATA ACQUISITION UNIT
118 DEGREE OF ATTENTION SETTING UNIT
120 STORAGE UNIT
121 SYMPTOMATIC ACTION DATABASE
122 AUTHENTICATION DATABASE
123 INDEX DATABASE
200 DISPLAY
300 VISIBLE LIGHT CAMERA
400 THERMAL CAMERA
900 FACILITY
N1 NETWORK
P1 PERSON
P2 PERSON

What is claimed is:

1. An image display apparatus comprising:
at least one memory storing instructions, and
at least one processor configured to execute the instructions to;
acquire a plurality of pieces of image data from a camera;
identify a person from the image data;
estimate a possibility of the person identified from the image data having developed an infectious disease;
detect an image of interest including a person of interest regarding which there is the possibility of the person of interest having developed an infectious disease and a nearby person present in the vicinity of the person of interest based on a result of the estimation;
extract a series of images including the image of interest; and
display the extracted series of images, wherein
a period, during which the series of images including the image of interest are extracted, is a period during which a first period, during which the person of interest is included in the series of images, overlaps with a second period, during which the nearby person is included in the series of images, and a preset period before and after the time when the image of interest has been captured.

2. The image display apparatus according to claim 1, wherein
the at least one processor is further configured to execute the instructions to acquire thermal image data from an infrared camera, and
estimate the possibility of the person having developed an infectious disease based on a body surface temperature of the person measured from the thermal image data corresponding to the image data.

3. The image display apparatus according to claim 1, wherein the at least one memory is further configured to store
a symptomatic action that is done when an infectious disease has been developed,
the at least one processor is further configured to execute the instructions to
detect an action done by the identified person, and
determine whether or not the detected action matches the symptomatic action, thereby estimating the possibility of the person having developed an infectious disease.

4. The image display apparatus according to claim 3, wherein
the at least one memory is further configured to store an action of coughing or an action of sneezing of the person as the symptomatic action, and
the at least one processor is further configured to execute the instruction to
detect the action of coughing or the action of sneezing of the person.

5. The image display apparatus according to claim 1, wherein
the at least one processor is further configured to execute the instruction to detect, as the image of interest, an image in which the person of interest and the nearby person are present at a distance less than a threshold from each other for a predetermined period or longer.

6. The image display apparatus according to claim 1, wherein
the at least one processor is further configured to execute the instructions to
detect an action of interest regarding the person of interest and the nearby person, the action of interest including at least one of movement of the mouth of the person, putting on a mask, coughing, sneezing, and coming into contact with each other, and
detect the image of interest based on the action of interest.

7. The image display apparatus according to claim 1, wherein
the at least one processor is further configured to execute the instructions to
take into account a degree of congestion of an area of an image of the image data including the person and then detect the image of interest.

8. The image display apparatus according to claim 1, wherein
the at least one memory is further configured to store an authentication data of the person and an attribute data of the person, and
the at least one processor is further configured to execute the instructions to
in addition to identifying the person, authenticate the person based on the authentication data, and
detect the image of interest based on the attribute data.

9. The image display apparatus according to claim 8, wherein
the attribute data includes antibody certificate data which the person has, and
the at least one processor is further configured to execute the instructions to
take into account the antibody certificate data of the person subjected to the authentication and then detect the image of interest.

10. The image display apparatus according to claim 1, wherein
the at least one memory is further configured to store an infection risk index related to a capturing place of the image data to be acquired,
the at least one processor is further configured to execute the instructions to
take into account the infection risk index related to the capturing place of the image data to be acquired and then detect the image of interest.

11. The image display apparatus according to claim 1, wherein
the at least one processor is further configured to execute the instructions to
detect an area of interest where the person of interest has stayed for a period longer than a preset period, and
detect an image in which the nearby person is present in the area of interest as the image of interest.

12. The image display apparatus according to claim 1, wherein
the at least one processor is further configured to execute the instructions to
acquire voice data in a capturing area of the image data, and
estimate the possibility of the person having developed an infectious disease based on a voice uttered by the person.

13. The image display apparatus according to claim 1, wherein
the at least one processor is further configured to execute the instruction to
detect the image of interest based on voices uttered by the person of interest and the nearby person.

14. The image display apparatus according to claim 1, wherein
the at least one processor is further configured to execute the instructions to
set a degree of attention in the image of interest based on a contact state between the person of interest and the nearby person,
output a series of images based on the degree of attention.

15. The image display apparatus according to claim 1, wherein
the at least one processor is further configured to execute the instructions to
estimate a risk of the nearby person being infected
set a degree of attention in the image of interest based on the risk of the nearby person being infected, and
output a series of images based on the degree of attention.

16. The image display apparatus according to claim 14, wherein
the at least one processor is further configured to execute the instructions to
set a priority of the series of images to be displayed so that it becomes higher as the degree of attention becomes higher, and
output the series of images set to be a first degree of attention in preference to the series of images set to be a second degree of attention, the first degree of attention being a relatively high degree of attention and the second degree of attention being a relatively low degree of attention.

17. An image display system comprising:
the image display apparatus according to claim 1; and
at least one of a camera configured to supply the image data to the image display apparatus configured to receive the series of images and display the received series of images.

18. An image display method executed by a computer, the image display method comprising:
acquiring a plurality of pieces of image data from a camera;
identifying a person from the image data;
estimating a possibility of the identified person having developed an infectious disease;
detecting an image of interest including a person of interest regarding which there is the possibility of the person of interest having developed an infectious disease and a nearby person present in the vicinity of the person of interest based on a result of the estimation; and
extracting a series of images including the image of interest and displaying the extracted series of images, wherein
a period, during which the series of images including the image of interest are extracted, is a period during which a first period, during which the person of interest is included in the series of images, overlaps with a second period, during which the nearby person is included in the series of images, and a preset period before and after the time when the image of interest has been captured.

19. A non-transitory computer readable medium storing a program for causing a computer to:
- acquire a plurality of pieces of image data from a camera;
- identify a person from the image data;
- estimate a possibility of the identified person having developed an infectious disease;
- detect an image of interest including a person of interest regarding which there is the possibility of the person of interest having developed an infectious disease and a nearby person present in the vicinity of the person of interest based on a result of the estimation; and
- extract a series of images including the image of interest and display the extracted series of images, wherein
- a period, during which the series of images including the image of interest are extracted, is a period during which a first period, during which the person of interest is included in the series of images, overlaps with a second period, during which the nearby person is included in the series of images, and a preset period before and after the time when the image of interest has been captured.

\* \* \* \* \*